United States Patent
Davies (10) Patent No.: US 6,553,987 B1
(45) Date of Patent: Apr. 29, 2003

(54) DRY POWDER INHALER

(75) Inventor: Michael Birsha Davies, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/857,761

(22) PCT Filed: Dec. 9, 1999

(86) PCT No.: PCT/EP99/09685

§ 371 (c)(1),
(2), (4) Date: Aug. 23, 2001

(87) PCT Pub. No.: WO00/35522

PCT Pub. Date: Jun. 22, 2000

(30) Foreign Application Priority Data

Dec. 11, 1998 (GB) ................................................ 9827200

(51) Int. Cl.[7] ........................ A61M 11/00; A61M 15/00; A61M 16/00; A61M 16/10; B05D 7/14; B65D 83/06

(52) U.S. Cl. ........................... 128/200.14; 128/200.12; 128/200.15; 128/200.17

(58) Field of Search ........................ 128/200.14, 203.15, 128/203.23, 203.12, 203.13, 203.21, 203.19, 203.24, 203.16, 203.17, 203.18, 203.2, 203.22, 200.15, 200.16; 604/58

(56) References Cited

U.S. PATENT DOCUMENTS

| | | | |
|---|---|---|---|
| 4,570,630 A | | 2/1986 | Elliott et al. |
| 5,082,148 A | * | 1/1992 | Dunning ................. 128/203.15 |
| 5,239,992 A | | 8/1993 | Behar et al. |
| 5,323,936 A | * | 6/1994 | Wolter et al. .......... 128/203.15 |
| 5,394,868 A | * | 3/1995 | Ambrosio et al. ...... 128/203.15 |
| 5,447,151 A | * | 9/1995 | Bruna et al. ........... 128/203.15 |
| 5,575,280 A | | 11/1996 | Gupte et al. |
| 5,765,552 A | * | 6/1998 | Zanen et al. ........... 128/203.12 |
| 5,996,577 A | * | 12/1999 | Ohki et al. ............. 128/203.12 |
| 6,029,661 A | * | 2/2000 | Whaley et al. ......... 128/203.15 |

FOREIGN PATENT DOCUMENTS

EP   0759 306 A   2/1997

* cited by examiner

Primary Examiner—Henry Bennett
Assistant Examiner—Kathryn Ferko
(74) Attorney, Agent, or Firm—James P. Rick (57) ABSTRACT

A metering device suitable for use in a dry powder inhaler comprises a housing defining a reservoir. The reservoir contains a powder. A rotatable auger, having a first and second end, has one or more flutes extending between the ends. The first end of the auger communicates with the reservoir. A dosing member, defining a dosing recess having a desired volume, is positionable adjacent said second end of said auger. Rotation of said auger causes the powder to be transferred through the flutes and into the dosing recess to fill the recess volume with a specific dose of powder.

22 Claims, 6 Drawing Sheets

DRY POWDER INHALER

This application is filed pursuant to 35 U.S.C. §371 as a United States National Phase Application of International Application No. PCT/EP99/09685 filed Dec. 9, 1999, which claims priority from GB9827200.8 filed Dec. 11, 1998.

The present invention relates to a dry powder delivery device, and in particular to a dry powder delivery device which has application in dry powder inhalers for delivering to a patient a metered dose of a pharmaceutical substance formulated in powder form.

BACKGROUND OF THE INVENTION

Delivery of therapeutic, prophylactic and diagnostic agents to the lungs of a patient may be accomplished using a variety of inhaler devices. One class of dry powder inhalers includes reservoir based dry powder systems. Reservoir based inhalers contain a bulk reservoir of a bioactive (therapeutic, prophylactic or diagnostic) agent suitable for inhalation, a mechanism for metering the bulk powder into individual doses, and a mechanism for aerosolising the dry powder into a patient's inhalation pathway for delivery to the lungs.

Reservoir based dry powder inhalers must operate within the constraints afforded by the use of bulk dry powders. For example, powders used within typical dry powder inhalers do not flow perfectly and always have a degree of cohesiveness. Thus, great care must be taken to ensure that powder flows within the device in order to assure that the powder reaches the appropriate point where it is metered. This is typically accomplished by blending the powder with an excipient, which is less cohesive and which allows the powder to flow. Excipients also act to dilute the active agent within the powder blend to allow more precise metering of potent active agents in an appropriate dose. Although excipients have several beneficial effects in terms of powder flow and metering, as a general rule, delivery of non-critical material is to be avoided. Thus, where possible, the better practice is to reduce the amount of non-essential excipient in a blend.

The flow of powders within inhaler devices may be effected by other mechanisms. For example, the movement of powder through a device to make it available for metering into doses may be assisted by applying a load to the powder within the reservoir. Such a load may be applied with a spring-biased plunger exerting pressure on the powder. The load biases movement of the powder towards the dosing mechanism in the device. This load mechanism can, however, create a compacting effect in the powder. The compacted powder may "bridge" at or near the dosing mechanism and therefore no longer flow as desired. Thus, it is desirable to avoid powder bridging.

An important consideration in a reservoir based dry powder inhaler is how the inhaler assures the accurate metering of the bioactive agent into doses, and assuring that this metering can be uniformly repeated within tight tolerances. In a reservoir based system, over-compaction of a therapeutic powder while metering a given dose or delivering multiple doses of powder to a patient where a single dose is intended may lead to an overdose. Depending on the agent being metered, an overdose may cause serious adverse side effects. Likewise, partial delivery or non-delivery of a dose of medication to a patient may fail to provide the desired therapeutic effect, also leading to potentially life-threatening situations, depending upon the condition being treated.

Reservoir based dry powder inhalers are well known in the art. For example, WO 92/18188 and WO 93/03782 disclose inhalers including powder reservoirs containing a pharmaceutical substance, generally combined with a powdered bulking agent. A dosing rod or shaft is moved within the reservoir in order to fill a metering recess therein. The rod or shaft is then pulled out of the reservoir in order to deliver the metered dose to an inhalation channel, where the dose can then be inhaled by the patient.

WO 92/04928 discloses an alternative reservoir based inhaler system in which the metering mechanism relies on a worm or auger positioned coaxially with the axis of the reservoir. A plunger in the device biases powder toward the end of the worm. The worm pushes out a "finger" of compacted powder at its opposite end that is then cut off at the end of a complete rotation. This "finger" provides the metered dose. Although the reference asserts that doses of precise size are delivered, there appears to be nothing to prevent the worm being repeatedly turned so that the patient could inhale a plurality of doses in a single inhalation. Moreover, the parallel and co-axial position of the worm within the reservoir potentially yields waste, due to the fact that when the coaxially aligned plunger abuts the end of the worm, it no longer biases the powder toward the auger. The remaining powder is no longer available for delivery to the patient, thus shortening the useful life of the device.

In contrast to the prior art devices, the aim of the present invention is to directly address the powder flow, powder content, dose accuracy and reproducibility concerns required for reservoir based dry powder systems. The present invention provides a novel metering system for dry powders having application in the area dry powder inhalers. In particular, the present invention provides a metering system for use in hand-held, dry powder reservoir based inhalers. The metering system may also be used in any instance where the accurate and reproducible metering of powders is desirable.

SUMMARY OF THE INVENTION

The present invention provides a dry powder metering system usable in dry powder inhalers comprising a housing, which has a walled portion defining a reservoir containing a powder. A bore intersects the reservoir at one end. A fluted auger positioned in the bore permits the transfer of powder through the bore. The auger communicates with a bore egress, where the powder is passed to a recess in a dosing member positioned adjacent to the bore egress. The dosing member recess is of a desired volume and the dosing member is moveable between a loading position adjacent the bore egress and a delivery position where the powder may be delivered.

The orientation of the reservoir to the auger within the bore is non-coaxial and non-parallel. Preferably, the axis of the reservoir is transverse to the axis of the auger, for example at approximately 90 degrees, with the reservoir only opening on to a portion of the cylindrical surface area of the auger, e.g. 50% or less than 50% of that surface area.

The auger and bore egress are designed such that rotation of the auger transfers powder into the dosing recess, but excessive rotation does not compact the powder at the dosing recess. The delivery of the powder to the recess may be made more reliable by increasing the volume of the bore egress to form an intermediate chamber. The intermediate chamber, which is later described in reference to the preferred embodiment, may act to even out cavitation within the powder and reduce the likelihood that dead space would be created within the dosing recess.

Thus, the present invention relates to a powder delivery device comprising a housing defining a reservoir, a bore and a bore egress, the reservoir having a top and a bottom and an axis therebetween. The bore extends into the housing from a bore egress, and the bore and the reservoir intersect at a bore/reservoir interface. The bore has an axis, which is non-parallel and non-coaxial with the axis of the reservoir. A rotatable auger is positioned coaxially within the bore. The auger has a spiral flute extending between the bore/reservoir interface and the bore egress. The delivery device may also have a dosing plate having a dosing recess for metering powder transferred from the bore egress.

The present invention also relates to a dry powder inhaler apparatus having an inhaler body with an air inlet, an air outlet, and an air flow pathway therebetween. The inhaler further comprises a walled portion defining a reservoir and a bore, the reservoir having first and second ends and an axis therebetween, the bore extending from a bore egress into the housing. The bore and the reservoir are in communication at one end of the reservoir at a bore/reservoir interface. The bore has an axis and the bore axis is non-parallel and non-coaxial with the axis of the reservoir. A rotatable auger is positioned coaxially within the bore. A spiral groove is defined in the auger. and the groove extends between the bore/reservoir interface and the bore egress. The inhaler also has a dose plate that has defined within it a dosing recess. The dose plate is movable between a loading position in which the dosing recess is in communication with the bore egress and a delivery position in which the dosing recess is in communication with the air flow pathway.

Additionally, the present invention relates to a method of delivering a powder to the respiratory tract of a patient comprising:

a. providing a dry powder inhaler having an air inlet, an air outlet and an air flow pathway defined therebetween, the inhaler further comprising:
   (i) a housing defining a reservoir and a bore, the reservoir having a top, a bottom and an axis therebetween, the bore extending from a bore egress into the housing, the bore and the reservoir in communication at the bottom of the reservoir at a bore/reservoir interface, the bore having an axis, the axis of the bore being non-parallel and non-co-axial with the axis of the reservoir;
   (ii) a powder positioned within the reservoir;
   (iii) an auger positioned within the bore, the auger being coaxialy rotatable within the bore, the auger having a spiral groove defined therein, the groove extending between the bore/reservoir interface and the bore egress;
   (iv) a dose plate defining a dosing recess, the dosing recess positioned adjacent the bore egress, the dosing recess exposable to the airflow pathway; and
b. rotating the auger to transport the powder from the reservoir into the auger groove and to the dosing recess.
c. Exposing the dosing recess to airflow pathway;
d. Creating an airflow in the airflow pathway; and
e. Entraining the powder contents of the dosing recess into the airflow to deliver the powder to the patient.

Thus, the present invention is based on the surprising realisation that bridging of powders may be reduced or avoided in a delivery device having an auger interfacing a reservoir in a non-parallel fashion. Thus orientation also allows the reservoir to be emptied of powder, thus minimising powder waste and maximising the useful life of the device. The orientation of the auger and reduction of potential bridging locations may also yield a benefit in permitting accurate delivery of less flowable powders, thus potentially allowing the use of powder blends with reduced course excipient to drug ratios.

Additionally, the present invention is based on the surprising realisation that an auger could be used to feed powder from a reservoir towards a dosing recess, with the amount of active agent metered remaining constant, regardless of the number of times the auger is rotated after the appropriate dose has been metered. It was to be expected that excessive turning of the auger would force powder from the reservoir towards the dosing recess and thus lead to an over compaction of the powder at that point. Surprisingly, however, it has been found by the inventors that the powder slips on itself, and that the dosing recess can reliably deliver a metered dose with only a predetermined minimum rotation of the auger. Accurate metering is thus not affected by excessive rotation of the auger.

Further still, the present invention is based on the surprising realisation that the inclusion of an intermediate chamber at the bore egress is useful in evening out cavitation and reducing dead space in a dosing recess, thus yielding a more even dosing of a metered powder.

These and other intentions and advantages will become apparent in the disclosure provided herein.

DESCRIPTION OF FIGURES

A preferred embodiment of the invention is described in more detail below, by example only, with reference to the following drawings wherein.

DESCRIPTION OF THE INVENTION

Figure 1:
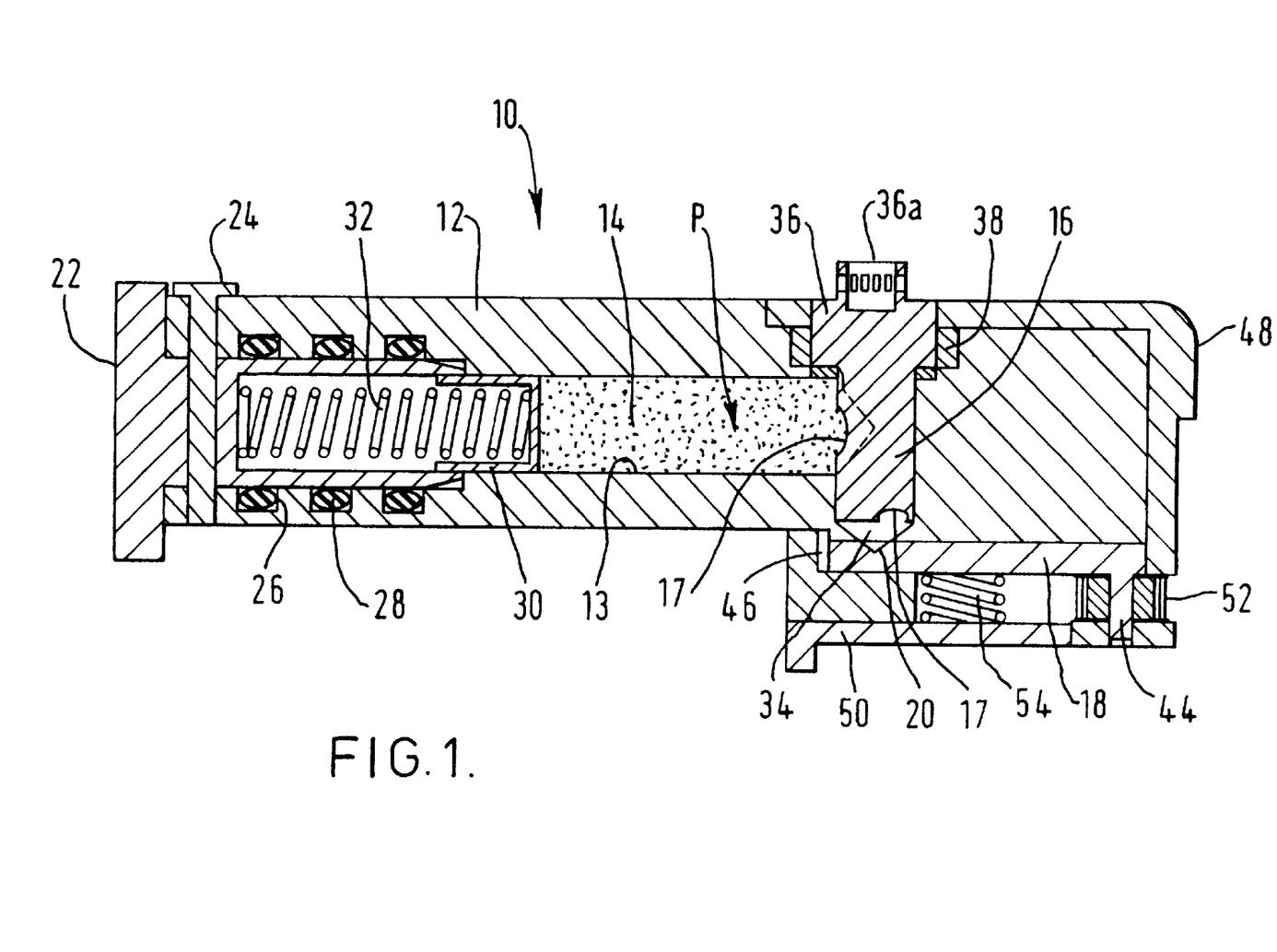
FIG. 1 is a sectional view of one embodiment of a device for metering powders in accordance with the present invention.
Figure 2:
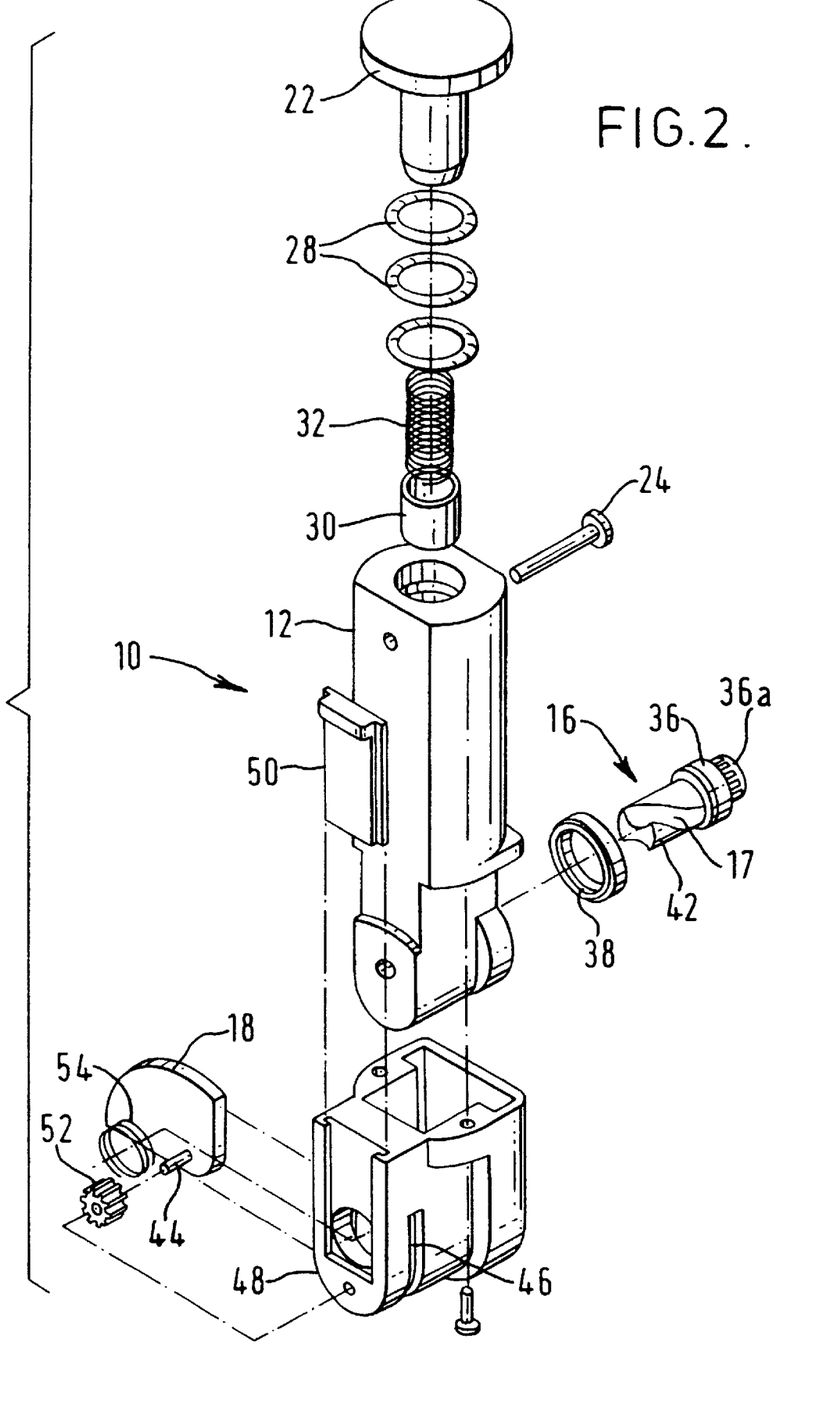
FIG. 2 is an exploded view of the device of FIG. 1.

A device for delivering powder in a dry powder inhaler is shown in FIGS. 1 and 2. Device 10 comprises a housing 12 which defines a walled portion 13 forming a reservoir 14 for a pharmaceutical powder P. The reservoir 14 communicates with a bore, in which lies an auger 16 having flutes 17. The intersection of the reservoir with the bore is referred to herein as the "bore/reservoir interface." The reservoir 14 of delivery device 10 contains a bulk amount of powder P. Auger 16 acts, as described later herein, to feed powder P towards a dose plate 18 in which is formed a dosing recess 20.

Reservoir 14 is elongate and extends transversely to the auger 16. The auger and the reservoir are therefore oriented in a non-parallel and non-coaxial fashion to each other. Preferably, as shown in FIG. 1, the reservoir and the auger are oriented at an angle of approximately 90 degrees to each other. It is believed that the parallel, non-co-axial arrangement of the auger and reservoir leads to a more even uptake of powder. As the edge of flute 17 is continually moving along the bore/reservoir interface, the likelihood that bridging will occur at the bore/reservoir interface is theoretically minimised, yielding increased flow of powder in the device.

In the preferred embodiment, reservoir 14 is circular in cross section and thus is basically cylindrical in shape. The width of the reservoir adjacent the auger is approximately the same as the diameter of the auger so that the reservoir opens on to approximately half the circumference of the auger. The equal sizing of the reservoir and auger diameters allows the contents of the reservoir to be emptied during use, thus minimising the amount of unusable powder in the reservoir.

At the one end of the reservoir there is a reservoir cap 22 fixed to housing 12 by means of a pin 24. Annular recesses 26 on the inside of the housing are for seals 28 which seal against the inner cylindrical part of the reservoir cap 22 to prevent the ingress of moisture and the egress of powder. A reservoir float or plunger 30 is located within the reservoir. The plunger is urged away from the cap 22 by a reservoir spring 32.

The powder is biased toward the bore/reservoir interface, and hence onto auger 16, by the pressure exerted by plunger 30. The spring characteristics are selected to urge the powder toward the interface but not to cause bridging of the powder.

In the embodiment described, auger 16 is between 4 mm to 10 mm in diameter, and is preferably approximately 6 mm in diameter. The auger's diameter, however, can be varied according to the requirements for which the device will be used. An auger cap 36 connects to auger 16, and the cap provides a suitable drive mechanism, such as gear 36*a*. Auger 16 is sealed within the housing 12 by means of a rotary seal 38. At least one and preferably two helical grooves or flutes 17 are located on opposite sides of auger 16. In one embodiment, each flute turns through approximately 90 degrees over the length of the auger. At any one time, the bottom of the reservoir 14 communicates with both a fluted part 17 of the auger and with a non-fluted part—a "land" 42. The number of flutes may be varied, as may their size, shape and pitch, as well as characteristics of their cutting edge or the ratio of flute area to land area.

The auger 16 is designed such that the powder in the bore egress 34 and in the dosing recess 20 is not over compacted, even after repeated turning of the auger. Thus, to provide a reliable metered dose of the powder, it is only necessary to turn the auger a predetermined minimum number of turns (for example three) but extra turns neither lead to excessive doses nor to compaction of the powder already at the dosing recess. The delivery device is thus relatively foolproof, as well as being relatively simple in construction.

The optimal characteristics of the auger will thus be determined by the physical characteristics of the powder P to be delivered, i.e., how cohesive it is. Powders tend not to be completely free flowing, and the pharmaceutical substance may only comprise a small proportion of the total blend. The cohesiveness of the powder in the blend may be a function of the cohesiveness the drug, or the bulking agent or both. With highly cohesive powders, a different design may be required than with relatively free flowing powders, for example, an increased flute size may be desired. The auger design should be chosen such that an efficient feeding of the powder from the reservoir to the dosing recess is achieved, but over compaction of the powder at the dosing recess does not occur upon repeated turning of the auger.

The powder, having flowed into the flutes of the auger under the biasing force of the plunger, is transported upon rotation of the auger in an archimedian screw-like fashion along the auger's length and into bore egress 34. The bore egress 34 is located at the terminal portion of the bore adjacent to and in communication with the dosing recess 20 of dose plate 18. In the preferred embodiment, the bore egress comprises a chamber between the flutes and the dosing recess and is referred to herein as an intermediate chamber.

The shape of the intermediate chamber 34 in the preferred embodiment is frusto-conical. The intermediate chamber is generally circular in cross section, to match the cross section of the auger, but has an inclined surface so as to lead directly to the profile of the rounded dosing recess 20. The chamber entry is thus the same relative diameter as the bore diameter, while its exit diameter is the same relative size as the opening to the dosing recess. The intermediate chamber is believed to serve several useful purposes. It is believed that it reduces cavitation within the chamber and distributes powder pressure such that uniform dosing is provided in the dosing recess. The presence of the intermediate chamber also avoids the formation of dead space (i.e., areas not actively filled by the powder exiting the rotating auger) in the dosing recess avoiding the risk that voids in the powder are created yielding under-dosing of the metered drug. In such case, it is surmised that powder exiting the flutes fills the intermediate chamber and dosing recess and that when the two are filled to capacity, the powder then slips on itself within the chamber between the flutes and the dosing recess, thus avoiding over compaction of the powder. As mentioned above, over compaction may theoretically yield delivery of more drug than desired to the dosing recess, creating the potential for over dosing.

When viewed from above, the dose plate 18 is approximately the shape of a quarter circle. The quarter circle has an angled corner and an arched hypotenuse across from the angled corner. A pivot pin 44, about which the dose plate pivots, is positioned at the angled corner and extends perpendicularly from the dose plate. The dosing recess 20 is positioned in the other side of the plate, in alignment with the bore egress. As shown in FIGS. 1 and 2, the housing 12 and dose plate 18 are positioned in a reservoir holder 48. The reservoir holder has formed within it a dosing slot 46. Pin 44 fitted on the front of the dose plate 18 extends through another recess in the reservoir holder 48. The holder 48 is closed at its forward face by means of a sliding front plate 50. A pivot gear 52 is mounted around pivot pin 44, within the reservoir holder 48. Dose plate spring 54 (FIG. 2) is mounted within an opening in the reservoir holder 48 and is compressed between the front plate 50 and the dose plate 18 to maintain plate 18 in a sealed orientation to housing 12.

As will be explained in more detain below, upon rotation of gear 52, dose plate 18 is pivotally rotated, causing dosing recess 20 to be moved away from bore egress 34 and through slot 46. The elongate shape of the dose plate allows the remaining surface of dose plate to cover the egress, preventing powder leakage. The plate may also act to prevent moisture ingress if fitted with appropriate sealing mechanisms or if constructed of or coated with a material that has sealing characteristics.

The delivery device described above can be used as a component in a dry powder medicament inhaler. This component can either be an integral part of the inhaler, or more appropriately, may be formed as a cassette which is inserted into an inhaler having a receiving dock, such as is represented in FIGS. 3–5.

Figure 3:
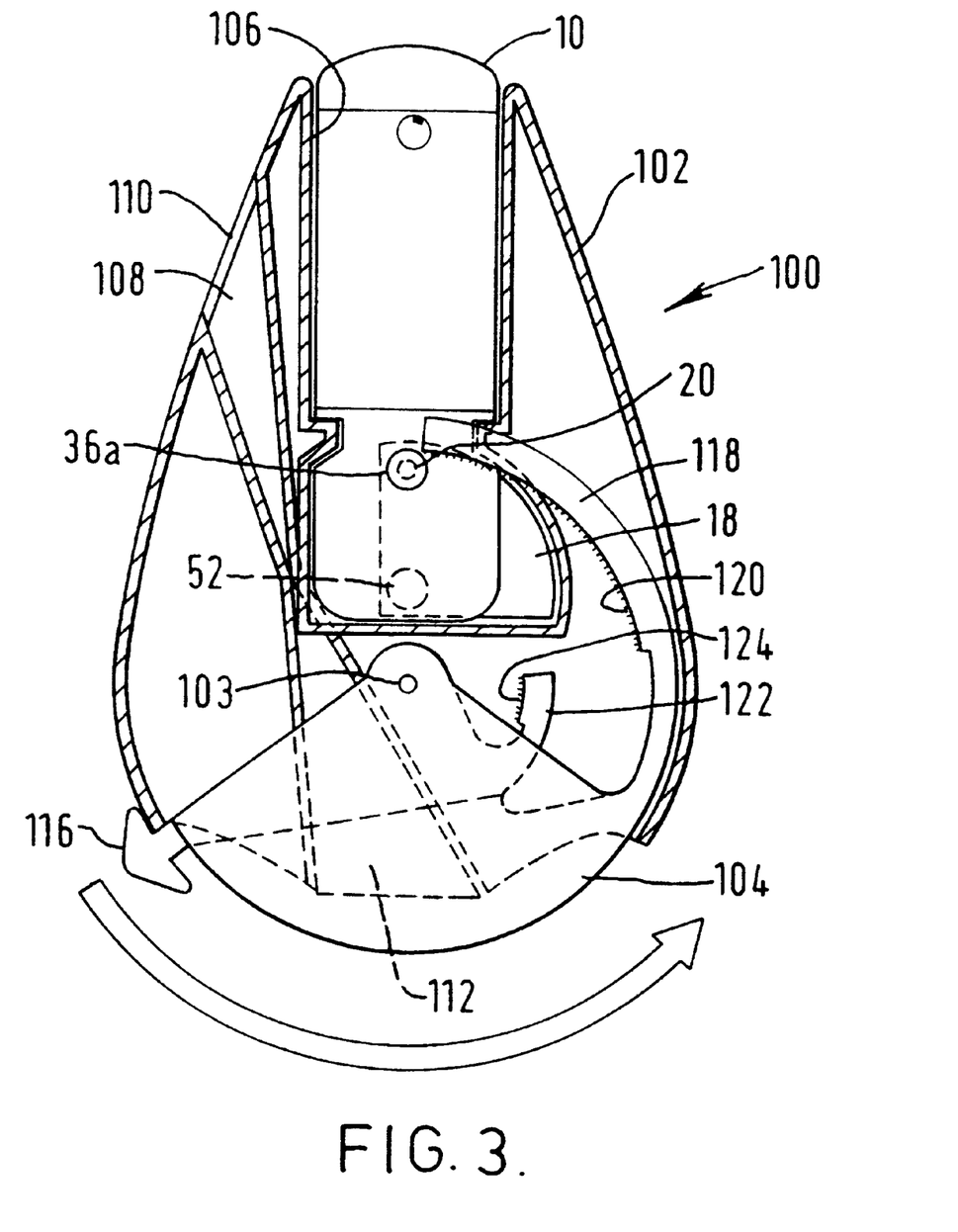
FIG. 3 is a sectional view of one possible powdered medicament inhaler incorporating the delivery device of FIG. 1, wherein the mouthpiece cover of the inhaler is closed and the dose plate is in the loading position.
Figure 4A:
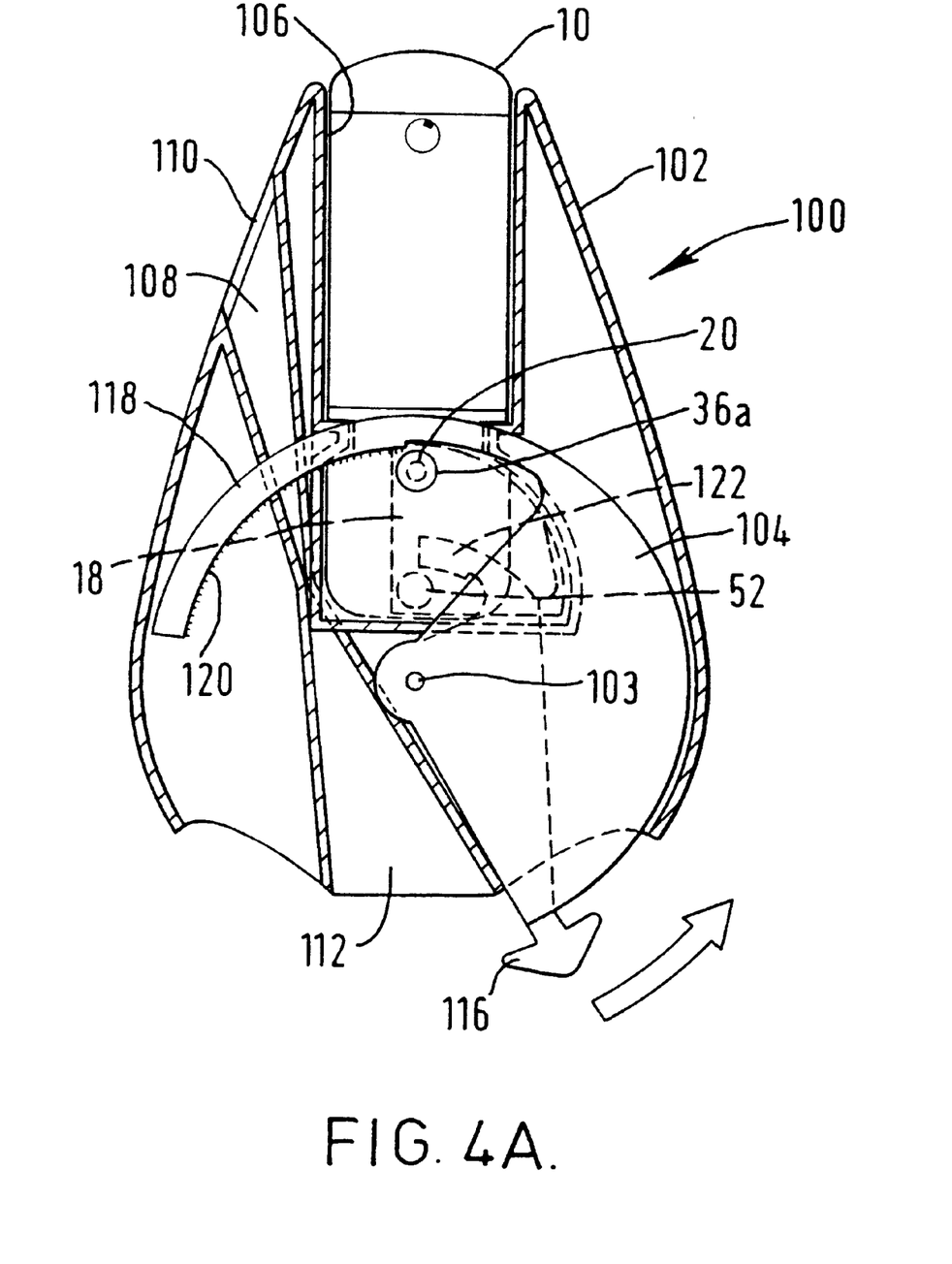
FIG. 4A is a top sectional view of the inhaler of FIG. 3 with the mouthpiece partially exposed.
Figure 4B:
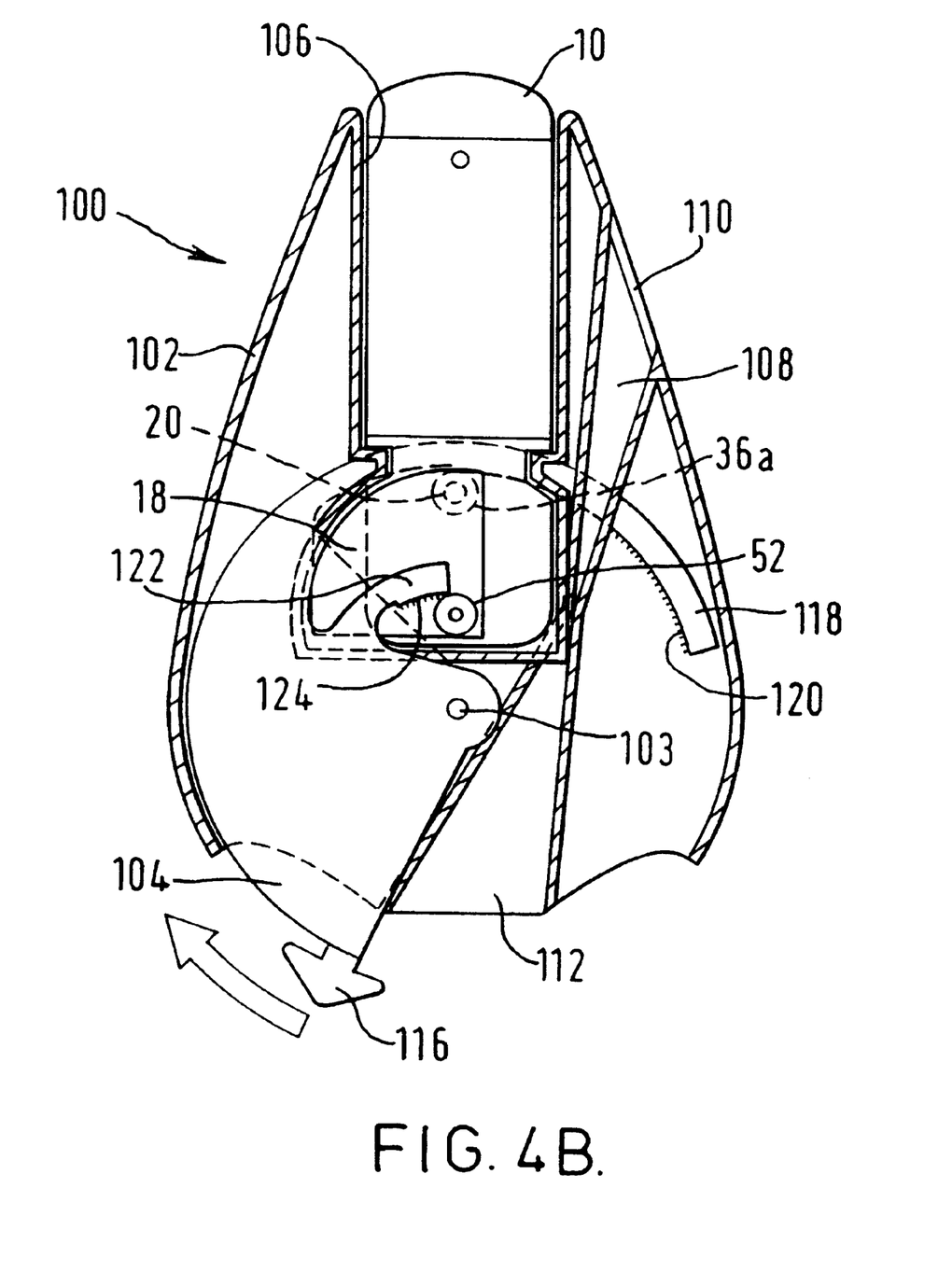
FIG. 4B is a bottom sectional view of the inhaler as shown in 4A.
Figure 5:
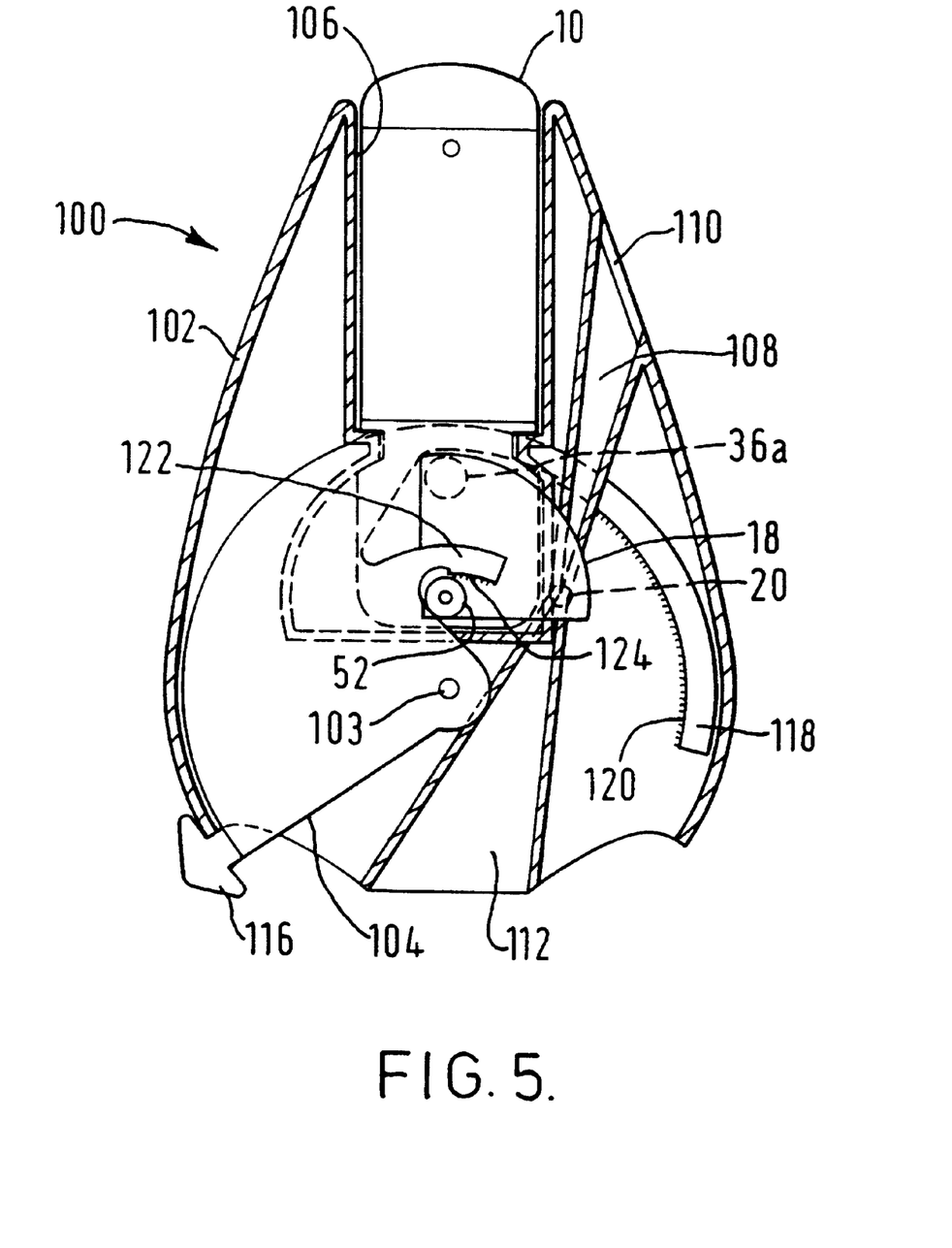
FIG. 5 is a bottom sectional view of the inhaler of FIG. 3 with the mouthpiece being fully exposed.

FIGS. 3–5 show a preferred powdered medicament inhaler of the present invention into which delivery device 10 has been inserted. In FIG. 3, inhaler device 100 comprises an outer inhaler body 102 and an integrated mouthpiece cover 104. Outer inhaler body 102 defines a delivery device dock 106 into which delivery device 10 has been inserted. The inhaler also defines an air-flow pathway 108 extending between an air inlet 110 and an air outlet in the form of a mouthpiece 112. The integrated mouthpiece cover 104 is slidably rotatable within the outer inhaler body 102, about a center of rotation 103. When the cover is closed, as depicted in FIG. 3, the integrated cover overlies mouthpiece 112. As the device is opened, the cover retracts inside the outer body, exposing mouthpiece 112.

The integrated mouthpiece cover 104 has a thumb grip 116 to assist in opening and closing the inhaler. The integrated mouth piece cover also carries a number of internal components which are not apparent from the external appearance of the inhaler. A curved auger gear arm 118 extends from the right upper side of the cover 104 and is situated so as to engage auger gear 36a of delivery device 10. To facilitate the complimentary engagement of the auger gear, gear arm 118 has a serrated portion 120 corresponding to the serrations on auger gear 36a. A dose plate transfer arm 122 extends from the lower right hand side of integrated mouthpiece cover 104. Dose plate transfer arm 122 also has a serrated portion 124, which is adapted to engage the dose plate pivot gear 52 of the delivery device 10 after a certain degree of rotation of integrated mouthpiece cover 104.

Although not shown, the integrated mouthpiece cover 104 may also be coupled to an air-flow path closure which is positioned to block the air flow pathway 108 when integrated mouthpiece cover 104 is closed. When the cover is opened, the closure would move out of the air-flow pathway 108 to permit inhalation through the device.

Description of the Delivery Device in Use

As mentioned above, the delivery device of the instant invention is designed to be an internal component of a dry powder inhaler, or more preferably to be a separate cassette, which can be inserted into a dry powder inhaler equipped with a cassette dock designed to receive such a device.

In the cassette version, one embodiment of which is depicted in FIGS. 3–5, the delivery device 10 is inserted into cassette dock 106 in outer inhaler body portion 102 of inhaler 100. So inserted, the delivery device is situated such that the auger gear 36a is aligned to be engaged by serrated portion 120 of auger gear arm 118, and the dose plate transfer arm 122 is aligned with the dose plate pivot gear 52.

As shown in FIG. 3, to open inhaler 100, a patient slides the thumb grip 116 across the inhaler in a counter-clockwise direction to expose mouthpiece 112, as represented by the arrows. The integrated mouthpiece cover 104 rotates within inhaler body 102, and the serrated portion 120 of the auger gear arm 118 engages the auger gear 36. The engaged arm causes the auger 16 (depicted in FIGS. 1 and 2) to turn within the bore of delivery device 10, thereby transferring powder from reservoir 14 into dosing recess 20 of dose plate 18 via flutes 17.

The integrated mouthpiece cover 104 is designed such that the serrated portion 120 of auger gear arm 118 is of an appropriate length to allow dosing recess 20 to be completely filled but that rotation of the auger ceases sometime after filling. The number of rotations the auger makes when the mouthpiece is retracted may readily be controlled by varying the diameter of the auger gear 36a, or by the adjusting the length of or number the serrated portion 120 of the auger gear arm 118 or number of serrations thereon.

FIG. 4A shows the relative position of the mouthpiece cover after the auger gear arm has disengaged the auger gear. From the bottom view depicted in 4B, it can be seen that further movement of the mouthpiece causes serrated portion 124 of dose plate transfer arm 122 to engage the dose plate pivot gear 52. Upon engagement of the dose plate pivot gear, dose plate 18 begins to pivotally rotate. Pivotal rotation of dose plate 18 moves the dosing recess 20 away from its loading position adjacent the egress of the bore. When this rotation is complete, the dosing recess 20 is in communication with the air flow pathway 108, and is said to be in its "delivery position" which is shown in FIG. 5.

Set to the position shown in FIG. 5, inhaler device 100 is held against the lips of the patient and the patient inhales through mouthpiece 112. Ideally, the inhaler would be held level by the patient so that the risk of powder spilling from the device would be minimized. Inhalation causes an air flow to be created in the air-flow pathway 108, entraining the contents of dosing recess 20 therein, and delivering a metered dose of powder P to the lungs of the patient.

To return the inhaler to the closed position, thumb grip 116 is slid in a closkwise direction causing integrated mouthpiece cover 104 to resume its original position wherein mouthpiece 112 is covered. This reverse rotation also returns dose plate 18 to the loading position. The inhaler is then ready for subsequent activation.

Powders Useful in the Device

The powder P contained within the reservoir can be any material which is desired to be metered. In the envisioned application for this delivery device the powder is a medicament to be delivered to a patient via an inhaler apparatus. Appropriate medicaments for delivery via the inhaled route may thus be selected from, for example: analgesics, e.g., codeine, dihydromorphine, ergotamine, fentanyl or morphine; anginal preparations, e.g., diltiazem; antiallergics, e.g., cromoglycate, ketoifen or nedocromil; antiinfectives, e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolilde, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, or (−)-4-amino-3,5-dichloro-α-[[[6-[2-(2-pyridinyl)ethoxy]hexyl]methyl] benzenemethanol; diuretics, e.g., amiloride; anticholergics, e.g., ipratropium, tiotroprium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines; diagnostics; and gene therapy agents. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimize the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

Indeed, it is envisioned, in accordance with this invention that any suitable diagnostic, prophylactic or therapeutic agent can be included as powder P within reservoir 14 of the present apparatus. Generally, drug particles suitable for delivery to the bronchial or alveolar region of the lung have an aerodynamic diameter of less than 10 micrometers. Other sized particles may be used if delivery to other portions of the respiratory tract is desired, such as the nasal cavity, mouth or throat. The medicament may be a pure drug, but more appropriately, it is preferred that powder P comprise a drug mixed with a bulking agent (excipient), for example, lactose.

Additional powders may be engineered with particular densities, size ranges or characteristics. Particles may comprise active agents, surfactants, wall forming materials, or other components considered desirable by those of ordinary skill.

Blends of bulking agents and drugs are typically formulated to allow the precise metering and dispersion on the powder into doses. A standard blend, for example, contains 13000 micrograms lactose mixed with 50 micrograms drug, yielding an excipient to drug ratio of 260:1. Because the present invention can meter and dispense such blends more accurately and effectively, dosage blends with excipient to drug ratios of 60:1, and potentially 2:1, may be used. At very low blend levels, however, the drug dose reproducibility becomes more variable.

Experimental Data

EXAMPLE 1

A metering apparatus was made as described above having a 6 mm diameter auger and a dosing recess of sufficient volume to hold 3 mg of powder. The device was filled with a micronized lactose and fluticasone propionate (FP) blend in a ratio of 60:1 (3000 parts lactose to 50 parts FP). Testing was conducted by rotating the auger a set number of rotations and then determining the amount of active agent in the dosing recess. Each rotation set was repeated approximately 10 times and results for each time taken. The average amount of active material for each set of rotations was taken, and RSD calculated. Testing was considered successful for dose uniformity if RSD was less than 10% for each set. The results shown in the following table indicate acceptable uniformity for a blend of 60:1.

| Number of turns | Average amount of drug in pocket | Range of Standard Deviation |
| --- | --- | --- |
| 0.5 | 26.2 | Within 10% |
| 1 | 35.1 | Within 10% |
| 3 | 63.6 | Within 10% |
| 5 | 61.6 | Within 10% |
| 10 | 58.2 | Within 10% |

Alternative Embodiments

The disclosure of the device provided above merely describes the preferred embodiment of the device. Alternative embodiments are considered to be within the scope of the present invention, as would be appreciated by those of ordinary skill in the art. For example, reservoir 14 could be of any shape or size. The reservoir could be circular or poly-angular in cross section. Relative to the size of the bore, the diameter of reservoir could be larger or smaller than the bore. Where larger than the bore/auger diameter, the floor of the reservoir could be tapered to interface with the auger.

As mentioned above, the auger/bore can be in any orientation which is non-parallel and non-coaxial with the axis of the reservoir. Although a tangential or perpendicular arrangement is preferred, the auger/bore may be angled toward or away from the end of the bore.

In the case where either reservoir shape or reservoir auger angle of orientation is different, the plunger 30 would ideally be adjusted to conform with the modified features. For example, in the case where the diameter of the reservoir was octagonal in cross-section, was larger than the bore diameter, had a tapered floor leading to the bore interface, and had an axis which intersected the axis of the bore/auger at 45 degrees (the auger sloping toward the dose plate recess), the plunger would also be octagonal in cross section to be in contact with the sides of the reservoir, it would be tapered corresponding to the taper of the floor of the reservoir, and it would be angled at 45 degrees to conform and align with the angle of the auger/bore axis.

The plunger 30 in the preferred embodiment is biased against the powder by spring 32. Alternatively, the plunger may be biased by mechanisms other than a spring. Any pressure creating means may be incorporated, for example a pressurised piston may be used. So configured, feeding mechanism for loading the dosing recess is functional in any orientation, and is not gravity dependent. Further, shaking or other agitation is not required.

The intermediate chamber utilised can be of any shape, size or volume which allows it to function as desired. The slope of the walls may be altered and it may be made larger or smaller than described in the preferred embodiment. The side of the intermediate chamber may also be parallel, or tapered in a reverse fashion from that shown in the preferred embodiment. Although the preferred bore egress comprises an intermediate chamber, it does not necessarily have to be so. The auger flutes may open directly into the dosing recess.

The location of the bore egress may also be modified. It is considered to be within the scope of the present invention that the bore egress could be located at any point along the length of the bore to which powder would be fed by the auger. If an intermediate chamber was positioned along the length of the bore, as opposed to the end of the bore as in the preferred embodiment, the chamber walls would be angled to conform with the curve of the bore. The egress to the recess would then be able to be flat in profile, which is believed to be the best configuration to allow the dose plate to be moved into the airflow path when incorporated into an inhalation device.

In the previously described preferred embodiment, the motion of the dosing member or dose plate was described as rotationally pivotal. It will be appreciated that a variety of motions could also be incorporated. For example, an alternative plate could be slid longitudinally into the airflow path. It could also be foreseen that the plate could be modified to eliminate the need to move the plate at all. For example, a closure could be provided between the bore egress and dose recess to close off the recess after it was filled, and a port on the opposite side the recess from the bore egress could be incorporated into the dose plate, which could then be opened to expose the metered dose to the airflow path.

It is also considered within the scope of the invention that the delivery device could be used as either a removable cassette unit that fits within a cassette dock of any number of devices or as a non-removable integral part of the inhaler, with the delivery device housing being formed by a walled portion of the inhaler.

Further still, the device may be used for delivery of medicaments via the mouth or nose, and thus the mouthpiece may actually comprise a nasal actuator.

The application of which this description and claims form part may be used as a basis for priority in respect of any subsequent application. The claims of such subsequent application may be directed to any feature or combination of features described herein. They may take the form of product, composition, process or use claims and may include, by way of example and without limitation, one or more of the following claims.

What is claimed is:

1. A metering device suitable for use in a dry powder inhaler comprising:
   a. a housing defining a reservoir, said reservoir containing a powder;
   b. a rotatable auger defining one or more spiral flutes; said auger having a first and second end and said one or more spiral flute extending therebetween, said first end in communications with said reservoir, and;
   c. a dosing member defining a dosing recess having a desired volume, said dosing recess positionable adjacent said second end of said auger;
      whereby rotation of said auger causes said powder to be transferred from said reservoir, through said flutes through said second end of said auger and into said dosing recess to fill said volume.

2. The device of claim 1 wherein the auger has a circumference and the reservoir interfaces with only a portion of the circumference of the auger at the bore/reservoir interface.

3. The device of claim 1 further comprising a plunger positioned within the reservoir and biased toward the auger.

4. The device of claim 1 wherein the bore extends through the housing, and auger has a drive at one end facilitating rotation of the auger.

5. The device of claim 1 wherein the powder is selected from the group consisting of therapeutic, prophylactic and diagnostic agents.

6. The device of claim 5 wherein the powder is selected from the group consisting of: analgesics, anginal preparations, anti-allergics, anti-infectives, antihistamines, anti-inflammatories, antitussives, bronchodilators, diuretics, anticholinergics, hormones, xanthines, therapeutic proteins and peptides, vaccines, and gene therapy agents.

7. The device of claim 6 wherein the powder is selected from the group consisting of: codeine, dihydromorphine, ergotamine, fentanyl, morphine, cephalosporins, penicillins, streptomycin, sulphonamides, tetrcyclines, pentamidine, diltiazem, cromoglycate, ketoifen, nedocromil, methapyrilene, beclomethasone dipropionate, fluticasone propionate, flunisolilde, budesonide, rofleponide, mometasone fuiroate, triamcinolone acetonide, noscapine, albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, (−)-4-amino-3,5-dichloro-α-[[[6-[2-(2-pyridinyl)ethoxy]hexyl]methyl] benzenemethanol, amiloride, ipratropium, tiotroprium, atropine, oxitropium, cortisone, hydrocortisone, insulin, glucagon, prednisolone, aminophylline, choline theophyllinate, lysine theophyllinate and theophylline.

8. A powder delivery device for dosing powder in a dry powder inhaler comprising:

a. an inhaler housing defining a reservoir, a bore and a bore egress, the reservoir having a first and a second end and an axis therebetween, the bore extending into the housing, and the bore and the reservoir in communication at the second end of the reservoir at a bore/reservoir interface, the bore having an axis, the axis of the bore being non-parallel and non-coaxial with the axis of the reservoir, the bore egress in communication with the bore; and b. a rotatable auger positioned coaxially within the bore, said auger suitable for delivering powder for dosation, the auger having a length, a flute at least partially spirally extending along a portion of said length, the flute allowing communication between the bore/reservoir interface and the bore egress.

9. The device of claim 8, wherein the reservoir axis is approximately perpendicular to the bore axis.

10. The device of claim 8, further comprising a dose plate defining a dosing recess, the dosing recess in communication with the bore egress.

11. The device of claim 10, wherein the dose plate is movable between a loading position wherein the dosing recess is adjacent the bore egress, and a delivery position wherein the contents of the recess may be removed.

12. The device of claim 11, wherein the dose plate is movable pivotally between the loading and delivery positions.

13. The device of claim 8, wherein the bore egress comprises an intermediate chamber.

14. The device of claim 13, wherein the intermediate chamber is tapers toward the dosing recess.

15. The device of claim 8 further comprising a powder within the reservoir.

16. A dry powder inhaler apparatus having an inhaler body with an air inlet, an air outlet, and an air flow pathway therebetween, and further comprising:
   a. a walled portion defining a reservoir and a bore, the reservoir having a first end and a second end and an axis therebetween, the bore extending from a bore egress into the housing, and the bore and the reservoir in communication at one end of the reservoir at a bore/reservoir interface, the bore having an axis, the axis of the bore being non-parallel and non-coaxial with the axis of the reservoir;
   b. a rotatable auger positioned coaxially within the bore, a spiral groove defined in the auger, the groove extending between the bore/reservoir interface and the bore egress; the direction of powder transfer is non co-axial with the plane of rotation of the auger; and
   c. a dose plate, said dose plate defining a dosing recess, the dose plate movable between a loading position, in which the dosing recess is in communication with the bore egress, and a delivery position in which the dosing recess is in communication with the air flow pathway.

17. The dry powder inhaler apparatus of claim 16, further comprising a loading arm capable of engaging the auger to cause rotation of the auger.

18. The dry powder inhaler apparatus of claim 16, further comprising a dose plate transfer arm capable of engaging the dose plate to move the dose plate between the loading and delivery positions.

19. The dry powder inhaler apparatus of claim 16, further comprising:
   a. an integrated mouthpiece cover positioned within the inhaler body, the integrated mouthpiece cover having a loading arm and a dose plate transfer arm, and wherein the integrated mouthpiece cover is moveable between a closed position, in which the dose plate is in the loading position, and an open position, in which the dose plate is in the delivery position and the dosing recess is in the air flow pathway.

20. The inhaler of claim 16, wherein the bore egress comprises an intermediate chamber.

21. A method of delivering a powder to the respiratory tract of a patient comprising:
  a. providing a dry powder inhaler having an air inlet, an air outlet and an air flow pathway defined therebetween, the inhaler further comprising:
    i. a housing defining a reservoir and a bore, the reservoir having a first and second end and an axis therebetween, the bore extending from a bore egress into the housing, the bore and the reservoir in communication at the second end of the reservoir at a bore/reservoir interface, the bore having an axis, the axis of the bore being non-parallel and non-co-axial with the axis of the reservoir,
    ii. a powder positioned within the reservoir,
    iii. an auger positioned within the bore, the auger being coaxially rotatable within the bore, the auger having a spiral groove defined therein, the groove extending between the bore/reservoir interface and the bore egress;
    iv. a dose plate, said dose plate defining a dosing recess, said dosing recess positioned adjacent the bore egress, and the dosing recess being exposable to the airflow pathway; and
  b. rotating the auger to transport the reservoir into the auger groove and into the dosing recess, such that the direction of powder transfer is non-coaxial with the lane of rotation of the auger;
  c. Exposing the dosing recess to airflow pathway;
  d. Creating an airflow in the airflow pathway, and
  e. Entraining the powder contents of the dosing recess into the airflow to deliver the powder to the patient.

22. A method for metering powders comprising:
  a. providing a metering device comprising:
    (i) a housing having reservoir, said reservoir containing a powder;
    (ii) a rotatable auger defining one or more spiral flutes; said auger having a first and second end and said flutes extending therebetween, said one or more flutes in communication with said reservoir and;
    (ii) a dosing member defining a dosing recess having a desired volume, said dosing recess positionable adjacent said second end of said auger;
  b. rotating said auger to cause said powder to move from said reservoir into said one or more spiral flutes and to move said powder through said flutes from said reservoir to said second end and into said dosing recess; and accessing said powder from said dosing recess.

* * * * *